United States Patent
Akada et al.

(10) Patent No.: US 6,608,009 B2
(45) Date of Patent: Aug. 19, 2003

(54) PHOSPHAZENE COMPOUNDS AND LUBRICANTS CONTAINING THE SAME

(75) Inventors: Tamio Akada, Kobe (JP); Yoshinobu Fujii, Kobe (JP); Nagayoshi Kobayashi, Kobe (JP); Rie Fujimoto, Kobe (JP)

(73) Assignee: Matsumura Oil Research Corp., Hyogo (JP)

( * ) Notice: Subject to any disclaimer, the term of this patent is extended or adjusted under 35 U.S.C. 154(b) by 0 days.

(21) Appl. No.: 10/101,496

(22) Filed: Mar. 20, 2002

(65) Prior Publication Data

US 2002/0183211 A1 Dec. 5, 2002

Related U.S. Application Data

(63) Continuation-in-part of application No. PCT/JP00/06368, filed on Sep. 19, 2000.

(30) Foreign Application Priority Data

Sep. 21, 1999 (JP) ............................................. 11-267696

(51) Int. Cl.$^7$ ....................... C10M 137/16; C07F 9/6521
(52) U.S. Cl. ........................ 508/422; 508/517; 508/582; 558/80; 428/694 BP; 428/694 BF
(58) Field of Search .......................... 508/422; 558/80; 428/694 BP (56) References Cited

U.S. PATENT DOCUMENTS

| | | | | |
|---|---|---|---|---|
| 3,207,776 A | | 9/1965 | Gilbert et al. .................. 260/461 |
| 4,613,548 A | * | 9/1986 | Lum .............................. 428/411.1 |
| 5,015,405 A | * | 5/1991 | Kar et al. ........................ 508/422 |
| 5,073,284 A | * | 12/1991 | Klobucar et al. ............... 252/78.5 |
| 5,225,549 A | | 7/1993 | Dekura ............................. 544/208 |
| 5,230,964 A | * | 7/1993 | Kar et al. ........................ 428/694 |
| 5,391,446 A | * | 2/1995 | Ohtani et al. ................... 430/58 |
| 5,441,655 A | * | 8/1995 | Odello et al. ................... 252/49.9 |
| 5,602,270 A | * | 2/1997 | Odello et al. ................... 558/80 |
| 5,705,668 A | * | 1/1998 | Odello et al. ................... 558/80 |
| 5,908,817 A | * | 6/1999 | Perettie et al. .................. 508/422 |
| 6,025,310 A | * | 2/2000 | Nishiguchi et al. ............ 508/582 |

FOREIGN PATENT DOCUMENTS

| | | |
|---|---|---|
| EP | 0 287 892 A2 | 10/1988 |
| WO | 98/18804 A1 | 5/1998 |

OTHER PUBLICATIONS

Elias, Anil J., et al.; "Polyfluoroalkoxy and Aryloxy Cyclic Phosphazenes: An Alternative Synthetic Route to Substitution Reactions Using Siloxanes in the Presence of Fluoride Ion Catalysts", *Inorganic Chemistry*; vol. 33, No. 13, pp. 2727–2734; 1994.

* cited by examiner

*Primary Examiner*—Ellen M. McAvoy
(74) *Attorney, Agent, or Firm*—Kubovcik & Kubovcik (57) ABSTRACT

A phosphazene compound of the formula (1) or (5) which has an arrangement such that perfluoroxyalkylene units selected from —CF$_2$O— and —CF$_2$CF$_2$O— are randomly distributed, the compound having a functional terminal group A or group G

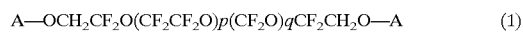
A—OCH$_2$CF$_2$O(CF$_2$CF$_2$O)$p$(CF$_2$O)$q$CF$_2$CH$_2$O—A (1)

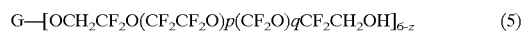

G—[OCH$_2$CF$_2$O(CF$_2$CF$_2$O)$p$(CF$_2$O)$q$CF$_2$CH$_2$OH]$_{6-z}$ (5)

wherein A is a group of the formula (a) and G is a group of the formula (g) shown in the specification, and a lubricant containing at least one of the phosphazene compounds of the formulas (1) and (5).

10 Claims, 6 Drawing Sheets

PHOSPHAZENE COMPOUNDS AND LUBRICANTS CONTAINING THE SAME

This application is a continuation-in-part of application of PCT/JP00/06368 filed Sep. 19, 2000.

BACKGROUND OF THE INVENTION

The present invention relates to a novel phosphazene compound and to a lubricant containing the phosphazene compound. More particularly the invention concerns with a compound to be used in a lubricant for a recording medium such as hard disks of large-capacity recording medium, and metal vapor-deposited tapes for 8 mm video tape recorder or digital video casette, and with a lubricant containing the compound.

Thanks to prevalent internet, intranet, local area network, etc, information can be fetched easily only by gaining access to a network. One of those which support this multimedia era is external recording devices. Of existing large-capacity external recording devices, those of the so-called CSS method are usually employed in which a recording medium layer is provided on a disk substrate having a high strength (hard disk), and the hard disk is rotated at high speed to operate a recording/reproducing element (head). Examples of the hard disk are a stationary magnetic disk, optical disk and optical magnetic disk. Of these, the most prevalent is a device employing the stationary magnetic disk. In order to increase the capacity of these external recording devices without changing their size, it is necessary to increase the surface recording density of a recording medium layer, for example. This requires that bit size be reduced and the head be brought near the recording medium as much as possible. To reduce a clearance between the head and disk, the unevenness of the disk surface should be minimized. For instance, to obtain a clearance of not more than 100 nm, the unevenness should be not more than 10 nm. However, if the smoothness of the disk surface is increased, the head is liable to be adsorbed onto the disk surface. To obtain high-speed response, it is necessary to increase bit transfer rate and therefore the rotational speed of the disk. For instance, a 3.5-inch hard disk requires a maximum number of revolution of 5400 to 7200 rpm, and the speed of the head as it passes through the periphery of the disk reaches 125 km/hr. Any of the above-mentioned modifications, however, increases considerably the probability of contact between the disk and head, as well as friction therebetween, thus decreasing the reliability.

In view of the foregoing, for protection of the disk surface and head, it is the simplest way to increase the amount of a lubricant applied to the surface of a protective coat for a disk. However, if the amount of a lubricant applied is increased, not only the slide resistance of the lubricant layer is increased but also the adsorption of the lubricant is enhanced, thereby causing a stop or burning of a spindle motor. For decreasing slide resistance, if used a lubricant of low viscosity, the lubricant moves and disappears from a protective layer during high-speed rotation of the disk. This causes a contact between the disk and head, and their breakage.

A lubricant, in an extremely simple manner, forms a lubricant film having a uniform thickness of molecules on a protective layer provided on a hard disk such as to reduce friction and wear which may be caused during the rotation of the hard disk and at the start and stop of the device. For protection of the disk and head, there is required a lubricant which has a low slide resistance, large bonding strength to a protective layer, low coefficient of friction, high chemical stability, high thermal stability, high corrosive resistance and lubricity at low temperatures of below −10° C., has a low vapor pressure, and which can form ultrathin films. A lubricant for hard disk is required to have no change in coefficient of friction over 50,000 times in CSS durability. That is, the lubricant should be free from abnormalities such as seizing of the head and blemish of the disk up to at least 50,000 times in a CSS repeated test.

From the point of view of chemical stability, strength, ultrathin film formation and smoothness, Diamond Like Carbon (DLC) is used in the surface protective layer of existing hard disks. This protective layer is, as apparent from its structure, mainly composed of carbon, which leads to a low chemical bonding. Its adhesion therefore merely depends upon hydrogen bond with hydrogen atom or nitrogen atom, and interaction such as van der Waals force.

Thus, perfluoroalkyl polyether oligomer (hereinafter referred to as "PFPE") is usually employed as a lubricant (Monthly magazine "Tribology", No. 99, November, pp37–38, 1995). PFPE has a low surface energy, chemical inertness, low vapor pressure, and thermal stability, which characteristics are derived from fluorocarbon. Unfortunately, it has a drawback that the bonding strength to the protective layer surface is small because of low surface energy, and the lubricant moves and disappears from the protective layer by centrifugal force during the rotation of a disk. To suppress this, an additive of a secondary component is used (U.S. Pat. No. 4,871,625), however, low compatibility deriving from the fluorocarbon of PFPE causes a phase separation, failing to obtain sufficient effect. In order to afford affinity in PFPE, there has been proposed one method in which a functional group, such as hydroxyl group or acylamide group, is introduced into the terminal or center of the main chain of PFPE (FOMBLIN Z Derivative, Ausimont S.p.A). Unfortunately, the functional group having such an active hydrogen might decrease chemical stability due to the friction with the head.

Perfluoroalkoxy phosphazene compounds are disclosed for treatment of magnetic recording medium (JP-A-63-103428). When these compounds are used as a lubricant for hard disks, the hard disks can not achieve sufficient CSS durability. Thus, there is a demand for a novel lubricant.

An object of the invention is to provide a compound to be used in a lubricant, e.g., for hard disks which have excellent CSS durability, and a lubricant containing such compound.

SUMMARY OF THE INVENTION

The present invention relates to a phosphazene compound of the formula (1) shown below which has an arrangement such that perfluoroxyalkylene units selected from —CF$_2$O— and —CF$_2$CF$_2$O— are randomly distributed, the compound having a functional terminal group A wherein A is a group of the formula (a) shown below, R is a hydrogen atom, C$_{1-4}$ alkyl, C$_{1-4}$ alkoxy, C$_{1-4}$ haloalkyl, aryl, substituted aryl, aryloxy or substituted aryloxy, and p and q are a real number of 1 to 30.

(a)

The present invention also relates to a phosphazene compound of the formula (5) which has an arrangement such that perfluoroxyalkylene units selected from —CF$_2$O— and —CF$_2$CF$_2$O— are randomly distributed, the compound having a functional terminal group G G—[OCH$_2$CF$_2$O(CF$_2$CF$_2$O)$p$(CF$_2$O)$q$CF$_2$CH$_2$OH]$_{6-z}$     (5)

wherein G is a group of the formula (g) shown below, R is a hydrogen atom, C$_{1-4}$ alkyl, C$_{1-4}$ alkoxy, C$_{1-4}$ haloalkyl, aryl, substituted aryl, aryloxy or substituted aryloxy, and p and q are a real number of 1 to 30, and z is an integer of 1 to 5.

(g)

The invention also concerns with a lubricant containing at least one of the phosphazene compounds of the formulas (1) and (5).

DETAILED DESCRIPTION OF THE INVENTION

Examples of C$_{1-4}$ alkyl are methyl, ethyl, propyl and butyl. Examples of C$_{1-4}$ alkoxy are methoxy, ethoxy, propoxy and butoxy. Examples of C$_{1-4}$ haloalkyl are fluoromethyl, trifluoromethyl, chloromethyl, fluoroethyl, trifluoroethyl, bromoethyl, iodopropyl, fluorobutyl, chlorobutyl and bromobutyl. Examples of aryl are phenyl and naphthyl. Examples of aryloxy are phenoxy and naphthoxy. Examples of substituents for substituted aryl and substituted aryloxy are C$_{1-4}$ alkyl, C$_{1-4}$ alkoxy and C$_{1-4}$ haloalkyl.

In the invention, the phosphazene compounds of the formulas (1) and (5) are novel compounds which are undisclosed in literature. For example, the compound is prepared from the oligomer of phosphonitrile halide, phenol and alcohol having hydroxyl groups introduced at both terminal ends of PFPE main chain. Examples of the oligomer of phosphonitrile halide are cyclic trimer of phosphonitrile chloride, cyclic tetramer of phosphonitrile chloride and mixtures thereof. Examples of phenol are phenol, meta-trifluoromethylphenol and like haloalkyl phenols, meta-methoxyphenol and like alkoxy phenols. Examples of alcohol having hydroxyl groups introduced at both terminal ends of PFPE main chain include the oligomer of perfluoroalkyl polyether of the formula (b) having an average molecular weight of 400 to 6000 (Ausimont S.p.A, Z Derivative):

HOCH$_2$CF$_2$O(CF$_2$CF$_2$O)$r$(CF$_2$O)$s$CF$_2$CH$_2$OH     (b)

wherein r is 1 to 30, and s is 1 to 30.

The compounds (1) and (5) of the invention can be prepared, for example, as follows. Phenol (alcohol) is reacted with sodium or the like to give phenolate (alcoholate), which is reacted with cyclic oligomer of phosphonitrile halide, as disclosed for example in JP-A-62-53996. Stated more specifically, phenol is dissolved in a solvent such as diethyl ether, diisopropyl ether or toluene. Then a reaction is conducted between the solution and a base such as metal sodium or sodium hydride in an amount smaller than an equivalent amount required for making the phenol entirely into phenolate, preferably 85 to 95% equivalent thereof at a temperature for refluxing the solvent until the base is entirely reacted, whereby phenolate is produced. The obtained phenolate is reacted with the cyclotrimer of phosphonitrile halide in an amount of 15 to 25% equivalent, preferably 18 to 21% equivalent, of the obtained phenolate to obtain aryloxy-substituted tricyclophosphonitrile halide. Separately alcohol having hydroxyl groups introduced at both terminal ends of PFPE main chain (hereinafter referred to as "PFPE-DOH") and the base selected from the above-mentioned bases are reacted in the same equivalent amount. The mixture is reacted at a temperature in the range from room temperature to 120° C., preferably 40 to 100° C. until the solid base can not be recognized. A reaction is conducted between the above-obtained aryloxy-substituted tricyclophosphonitrile halide and the alcoholated PFPE-DOH in an ether solvent such as diethyl ether, diisopropyl ether or perfluorohexyl methyl ether for 1 to 10 days, preferably for 2 to 5 days at a temperature in the range from room temperature to the solvent-refluxing temperature. The thus-obtained reaction mixture is added to the ether solvent solution containing the phenolate separately prepared. The mixture is reacted for 5 to 15 days at a temperature in the range from room temperature to the solvent-refluxing temperature, preferably at the solvent-refluxing temperature until the partially halogen-substituted tricyclophosphonitrile can not be detected. The thus-obtained reaction mixture is washed with water a few times, dehydrated and dried after which the solvent used is removed by distillation under reduced pressure. When the obtained reaction mixture contains unreacted phenol, PFPE-DOH and hexaaryloxy-substituted tricyclophosphonitrile, these substances are removed from the reaction mixture by molecular distillation, whereby the compound (1) is produced.

The reaction system of the invention may contain higher molecular weight compounds like those of the formula (2) and the formula (3) as shown below, as well as the compound of the formula (1). The lubricant of the invention may include small amounts of such compounds. B in the formulas (2) and (3) represents a group of the formula (4).

(2)

(3)

—CH$_2$CF$_2$O(CF$_2$CF$_2$O)$r$(CF$_2$O)$s$CF$_2$CH$_2$—   (4)

wherein r is 1 to 30 and s is 1 to 30.

The compound of the formula (1) can be prepared as described above. The compound of the formula (5) can be prepared by terminating the reaction at a suitable time instead of waiting until completion of the reaction.

The compounds (1) and (5) of the invention are suitable for use as an incombustible lubricating oil, a hydraulic oil or the like, particularly as a lubricant for a recording medium.

In use as a lubricant, the phosphazene compound of the invention can be employed as a lubricant by itself but may be used as dissolved in an appropriate organic solvent. Examples of the organic solvent are toluene, xylene and like aromatic hydrocarbons, methylene chloride, chloroform, 1,1,1-trichloroethane, 1,1,2-trichloroethane, trichlorotrifluoroethane (CFC-113), perfluorohexyl methyl ether (HFE-7100) and like halogenated hydrocarbons, diethyl ether, dimethoxyethane, dioxane, tetrahydrofuran and like ethers, ethyl acetate, butyl butyrate, amyl acetate and like esters, cyclohexane, cycloheptane, cyclooctane and like alicyclic hydrocarbons, dimethylformamide, dimethyl sulfoxide, and mixtures of two or more kinds of these solvents.

When the lubricant of the invention is used for a recording medium, at least one of the compounds of the formulas (1) and (5) are used in a concentration of about 0.1% by weight or more, usually about 0.1 to about 100% by weight, preferably about 10 to about 100% by weight, more preferably about 20 to about 100% by weight.

In the invention, at least one of the compounds of the formulas (1) and (5) can be used in combination with the oligomer of perfluoroalkyl polyether of the formula (b) having an average molecular weight of 400 to 6000

HOCH$_2$CF$_2$O(CF$_2$CF$_2$O)$r$(CF$_2$O)$s$CF$_2$CH$_2$OH   (b)

wherein r is 1 to 30, and s is 1 to 30.

In the invention, at least one of the compounds of the formulas (1) and (5) can be used in combination with the oligomer of perfluoroalkyl polyether of the formula (c)

X—CF$_2$O(CF$_2$CF$_2$O)$m$(CF$_2$O)$n$CF$_2$—Y   (c)

wherein X and Y are each at least one group selected from HO(CH$_2$CH$_2$O)$t$CH$_2$—, HOCH$_2$CH(OH)CH$_2$OCH$_2$—, HOOC— and piperonyl, m is 1 to 80, n is 1 to 80, and t is 1 to 30.

Examples of the oligomer (c) are those commercially available under FOMBLIN ZDo1-TX, Z-TETRAOL, Z-DIAC and AM3001 (products of Ausimont S.p.A).

In the invention, at least one of the compounds of the formulas (1) and (5) can be used in combination with the oligomer of perfluoroalkyl polyether of the formula (d)

F—[CF(CF$_3$)CF$_2$O]$u$CF(CF$_3$)COOH   (d)

wherein u is 1 to 60.

Examples of the oligomer (d) include a compound commercially available under KRYTOX 157FS (E.I. du Pont de Nemours and Co.).

In the invention, at least one of the compounds of the formulas (1) and (5) can be used in combination with the phosphazene compound of the formula (e)

[N=P{OCH$_2$CF$_2$CF$_3$}$a${OCH$_2$(CF$_2$CF$_2$)$x$H}$b$]$y$   (e)

wherein a and b are each a real number of 0 to 2, a+b=2, x is 1, 2, 3 or 4, and y is 3 or 4. Examples of the phosphazene compound (e) are those commercially available under MORESCO PHOSPHALOL NF-100 and NF-46 (Matsumura Oil Research Corp).

When the compound (b), (c), (d) or (e) is used in combination with at least one of the compound of the formula (1) and (5), each compound is used in a concentration of 0.1% by weight or more, preferably about 10 to about 90% by weight. At least two kinds of compounds (b), (c), (d) and (e) can be used in combination with at least one of the compound of the formula (1) and (5).

DETAILED DESCRIPTION OF PREFERRED EMBODIMENTS

The invention will be described in more detail with reference to the following examples to which, however, the invention is not limited. All of reactions described hereinafter were carried out in an atmosphere of argon gas.

EXAMPLE 1

A 2-liter 4-necked flask equipped with a reflux condenser, an argon gas inlet tube, a thermometer and a stirrer was charged with 282.1 g (1.74 moles) of meta-trifluoromethylphenol and 1.2 liters of diisopropyl ether which was dried, dehydrated and purified by distillation. Then 36.5 g (1.59 moles) of small pieces of metal sodium was added with stirring. A reaction was conducted at a temperature for refluxing the diisopropyl ether for two days. After confirming that the metal sodium was entirely consumed, 107.7 g(0.31 mole) of cyclotrimer of phosphonitrile chloride was added while stirring the reaction mixture. Thereafter a reaction was made at a refluxing temperature for 3 days to give about 1300 g of a reaction mixture. The reaction mixture was washed with about 500 ml of purified water 5 times. Then the diisopropyl ether layer was separated and dehydrated by molecular sieves after which the diisopropyl ether was removed under reduced pressure by distillation with a rotary evaporator, giving a brown transparent liquid, which is hereinafter referred to as "(i)".

A flask of the same type as above was charged with 144.4 g (0.151 mole) of PFPE-DOH (alcohol wherein the average values of r and s in the formula (b) are 1 and 10, respectively) and 3.5 g (0.151 mole) of small pieces of metal sodium. The mixture was reacted at 50 to 100° C. for 12 days. Then it was confirmed that the metal sodium was entirely consumed in the reaction. Thereafter 450 g of perfluorohexyl methyl ether was added to reduce the viscosity of the reaction mixture. A solution of 150.5 g of the liquid (i) in 140 g of diisopropyl ether was gradually added dropwise to the mixture. After 3-day stirring at a refluxing temperature, the mixture was left to cool to room temperature, giving a reaction mixture (which is hereinafter referred to as "(ii)").

Using 230 g of perfluorohexyl methyl ether, the total amount of the reaction mixture (ii) was quantitatively added to a solution containing 700 g of diisopropyl ether and 1.19 moles of meta-trifluoromethyl phenolate separately prepared from 192.7 g (1.19 moles) of meta-trifluoromethylphenol and 24.8 g (1.08 moles) of small pieces of metal sodium in the same manner as in preparation of the liquid (i). The mixture was reacted by 9-day stirring at a temperature for refluxing the solvent. After confirming by capillary gas chromatography that the reaction mixture did not contain cyclotrimer of phosphonitrile wherein meta-trifluoromethylphenoxy group and chlorine atom alone were substituted as mixed together, namely did not contain any reaction intermediate, the contained solvent was distilled off from the reaction mixture under reduced pressure by a rotary evaporator. The obtained residue was dissolved in 200 g of diethyl ether. The diethyl ether solution was washed successively with 200 g of 1% aqueous solution of nitric acid three times and with 200 g of purified water four times. After these operations, the diethyl ether layer was dehydrated and dried by molecular sieves. The diethyl ether was vaporized for removal by a rotary evaporator under reduced pressure, giving 222.6 g of a slightly turbid oily liquid. It was confirmed by capillary gas chromatography that the reaction product contained, as a by-product, cyclotrimer of phosphonitrile wherein 6 meta-trifluoromethylphenoxy groups were substituted and an unreacted PFPE-DOH. In view of this, these compounds were separated by a molecular distiller equipped with a diffuser pump, thereby producing 12 g (0.004 mole) of a pale yellow transparent liquid.

The obtained product was identified as the following substance according to a ratio of methylene proton and aromatic proton based on meta-trifluoromethylphenoxy group in proton NMR (400 MHz) and according to FT-IR:

[compound (1-a)], density 1.7 g/cm$^3$ (15° C.), boiling point 170° C. or higher/10$^-$torr, viscosity (dynamic viscosity) 180 mm$^2$/sec (40° C.), surface tension 30.2 dyne/cm (25° C.).

EXAMPLE 2

Using meta-phenoxyphenol in place of meta-trifluoromethylphenol used in Example 1, the same reaction as in Example 1 was conducted, giving 270.6 g of an oily liquid containing cyclotrimer of phosphonitrile wherein 6 meta-phenoxyphenoxy groups were substituted (by-product) and unreacted PFPE-DOH. Then, 50 g of toluene was added to the oily liquid and was stirred. The mixture was placed into a separating funnel and left to stand therein overnight for separation of two layers. After confirming that the most of cyclotrimer of phosphonitrile having 6 meta-phenoxyphenoxy groups substituted was extracted in the upper toluene layer, the lower layer was distilled by a molecular distiller equipped with a diffuser pump. Thereby the residue was separated from toluene, the portion of cyclotrimer of phosphonitrile having 6 meta-phenoxyphenoxy groups substituted which was not extracted in the toluene layer, and unreacted PFPE-DOH, giving 23 g (0.007 mole) of yellow transparent liquid.

The obtained product was identified as the following substance according to a ratio of methylene proton and aromatic proton based on meta-phenoxyphenoxy groups in proton NMR (400 MHz) and according to FT-IR:

$(C_6H_5OC_6H_4O)_5P_3N_3OCH_2CF_2(OCF_2CF_2)(OCF_2)_{10}OCF_2CH_2ON_3P_3(OC_6H_4OC_6H_5)_5$

[compound (1-b)], density 1.6 g/cm$^3$ (15° C.), boiling point 200° C. or higher/10$^{-4}$ torr, viscosity (dynamic viscosity) 380 mm$^2$/sec (40° C.), surface tension 31.5 dyne/cm (25° C.).

COMPARATIVE EXAMPLE 1

Compound Disclosed in JP-A-6-220077

A 1-liter 4-necked flask equipped with a reflux condenser, an argon gas inlet tube, a thermometer and a stirrer was charged with 41.3 g (0.083 mole) of $C_3F_7O(CF_2CF_2O)_2CF_2CH_2OH$ and 0.5 liter of diisopropyl ether which was dried, dehydrated and purified by distillation. Then 1.73 g (0.075 mole) of small pieces of metal sodium were added under stirring. A reaction was conducted at a temperature of 50° C. for 3 days. After the entire metal sodium was reacted, 6.95 g (0.02 mole) of cyclotrimer of phosphonitrile chloride and 40 ml of diisopropyl ether were added. The mixture was reacted at 60 to 70° C. for 2 days, giving a reaction mixture which is hereinafter referred to as "(iii)".

In the same manner as in preparation of (iii), 18.8 g (0.198 mole) of phenol and 4.14 g (0.18 mole) of metal sodium were reacted in 250 ml of diisopropyl ether for 5 days, giving a solution of sodium phenolate in diisopropyl ether, which is hereinafter referred to as "(iv)".

The total amount of (iv) was poured into a flask containing the reaction mixture (iii) at room temperature over a period of about 5 minutes. A reaction was conducted at 70° C. for 10 days. A solution of the reaction mixture in diisopropyl ether was washed successively with an aqueous solution of sodium hydroxide, with an aqueous solution of nitric acid 4 times, and with purified water 6 times. The diisopropyl ether solution obtained by these washing operations was dehydrated and dried by molecular sieves. Thereafter the diisopropyl ether was removed by distillation with a rotary evaporator under reduced pressure, giving 23.3 g of a pale yellow liquid.

The obtained product was identified as the following substance according to a ratio of methylene proton and aromatic proton based on phenoxy group in proton NMR (400 MHz) and according to FT-IR:

[compound (D)], density 1.6 g/cm$^3$ (15° C.), viscosity (dynamic viscosity) 50 mm$^2$/sec (40° C.), surface tension 25.2 dyne/cm (25° C.).

EXAMPLE 3

A hard disk was immersed in a solution of 1 g of the compound (1-a) obtained in Example 1 in 1000 ml of perfluorohexyl methyl ether (HFE-7100), was taken out and dried at 120° C. for 30 minutes, whereby a coating film of 10 angstroms in thickness was formed on the hard disk. The coated hard disk was subjected to the following test.

In the performance test of lubricants, a modified commercially available drive was used such that coefficient of friction was determined from the force applied to the head, and the test was carried out by measuring the change in coefficient of friction in a CSS repeated test. A single CSS cycle took 33 seconds which comprises the steps of starting the drive with the head contacted on the disk surface, rotating the disk such as to reach a predetermined number of revolution of 7200 rpm with the head lifted, and stopping the drive with the head contacted with the disk surface. The hard disk was obtained by forming, with plasma CVD, a DLC protective layer of 100 to 200 Å on a 3.5-inch recording medium prepared by sputtering. For increasing the surface smoothness, no texture was used. The head was of monolithic MIG (metal in gap), and the load was 7.5 g. A CSS test was conducted for evaluation based on the number of cycles until the head adhered (crushed) to the disk (CSS life) and the state of disk (occurrence or non-occurrence of abrasion).

The result was that the CSS life was 50000 cycles or more and the state of disk was not abnormal.

EXAMPLE 4

The test was carried out in the same manner as in Example 3 with the exception of using 1 g of the compound (1-b) in place of 1 g of the compound (1-a). The result was that the CSS life was 50000 cycles or more and the state of disk was not abnormal.

EXAMPLE 5

The test was carried out in the same manner as in Example 3 with the exception of using 0.2 g of the compound (1-a) and 0.8 g of oligomer of perfluoroalkyl polyether having an average molecular weight of 2000 (product of Ausimont S.p.A, Z Derivative), in place of 1 g of the compound (1-a). The result was that the CSS life was 50000 cycles or more and the state of disk was not abnormal.

COMPARATIVE EXAMPLE 2

The test was carried out in the same manner as in Example 3 with the exception of using 1 g of the compound (D) in place of 1 g of the compound (1-a). The result was that the CSS life was 28000 cycles and the disk had abrasion.

JP-A-6-220077 discloses the compound of chemical structure prepared in Comparative Example 1 (described herein). The disclosed compound is similar to the compound of the formula (1) according to the invention. However, this publication does not disclose the usefulness of the compound as a lubricant for a recording medium. It is clear from comparison of Examples 3 and 4 (described herein) with Comparative Example 2 (described herein) that the compound described in JP-A-6-220077 is not useful as a lubricant for a recording medium in the aspect of performance.

EXAMPLE 6

The reactions were conducted in the same manner as in Example 1 except of using 302 g (0.151 mole) of PFPE-DOH (alcohol having an average molecular weight of 2000 and the average values of r and s in the formula (b) are 10.8 and 9.7, respectively in place of 144.4 g (0.151 mole) of PFPE-DOH (alcohol wherein the average values of r and s in the formula (b) are 1 and 10, respectively, to obtain 350 g of a slightly turbid oily liquid instead of 222.6 g of a slightly turbid oily liquid.

From the oily liquid was removed by washing with toluene a by-product, cyclotrimer of phosphonitrile wherein 6 meta-trifluoromethylphenoxy groups were substituted, giving 270 g of yellow transparent liquid. The liquid was extracted with use of carbon dioxide in supercritical state to separate 60 g (0.015 mole) of compound (1-c) and 80 g (0.027 mole) of compound (5-a).

[compound (1-c)], density 1.69 g/cm³ (15° C.), boiling point 170° C. or higher/10⁻⁴ torr, viscosity 340 cps (40° C.), surface tension 31 dyne/cm (20° C.).

[compound (5-a)], density 1.75 g/cm³(15° C.), boiling point 170° C. or higher/10⁻⁴ torr, viscosity 110 cps (40° C.), surface tension 23 dyne/cm (20° C.).

The obtained product was identified as the following substance according to proton NMR (400 MHz) and FT-IR:

The compound (1-c) was a compound having a cyclotrimer of phosphonitrile wherein 5 meta-trifluoromethylphenoxy groups substituted on both ends of PFPE-DOH.

The compound (5-a) was a compound having a cyclotrimer of phosphonitrile wherein 5 meta-trifluoromethylphenoxy groups substituted on one end of PFPE-DOH.

Figure 1:
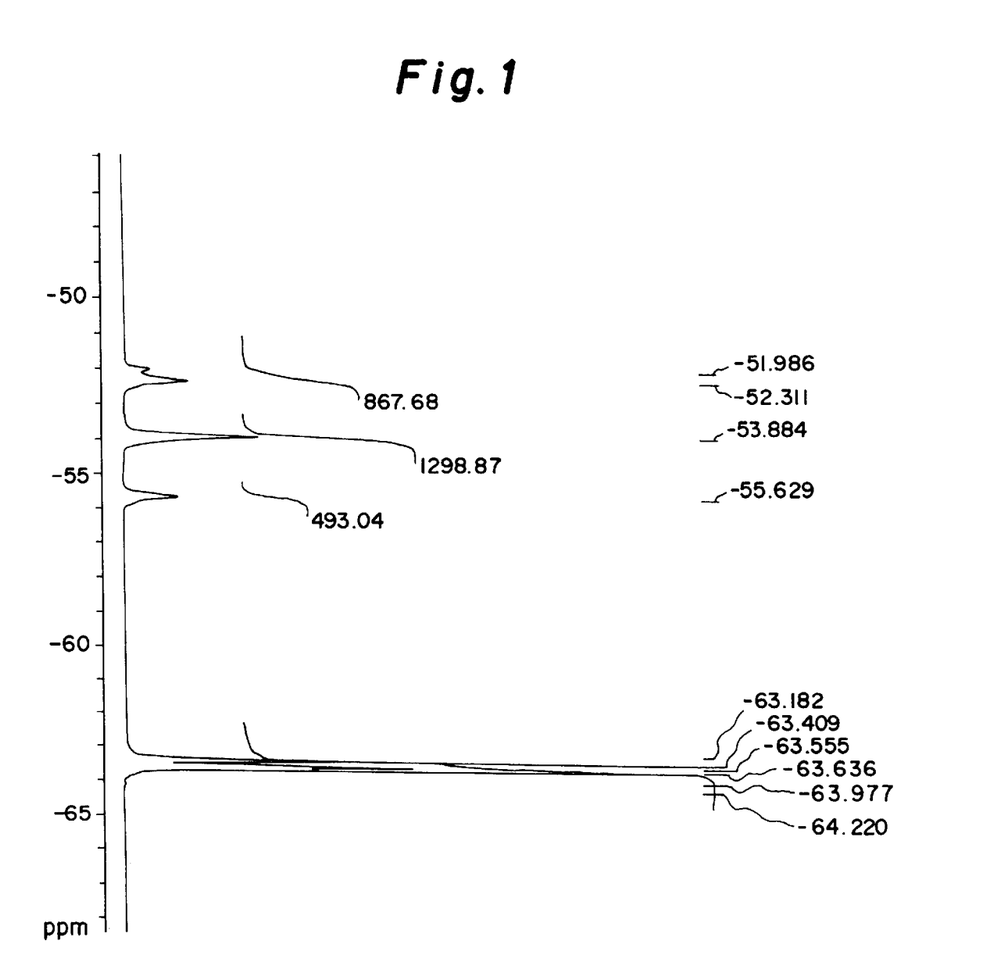
FIGS. 1 to 3 are NMR charts of the compound (1-c).
Figure 2:
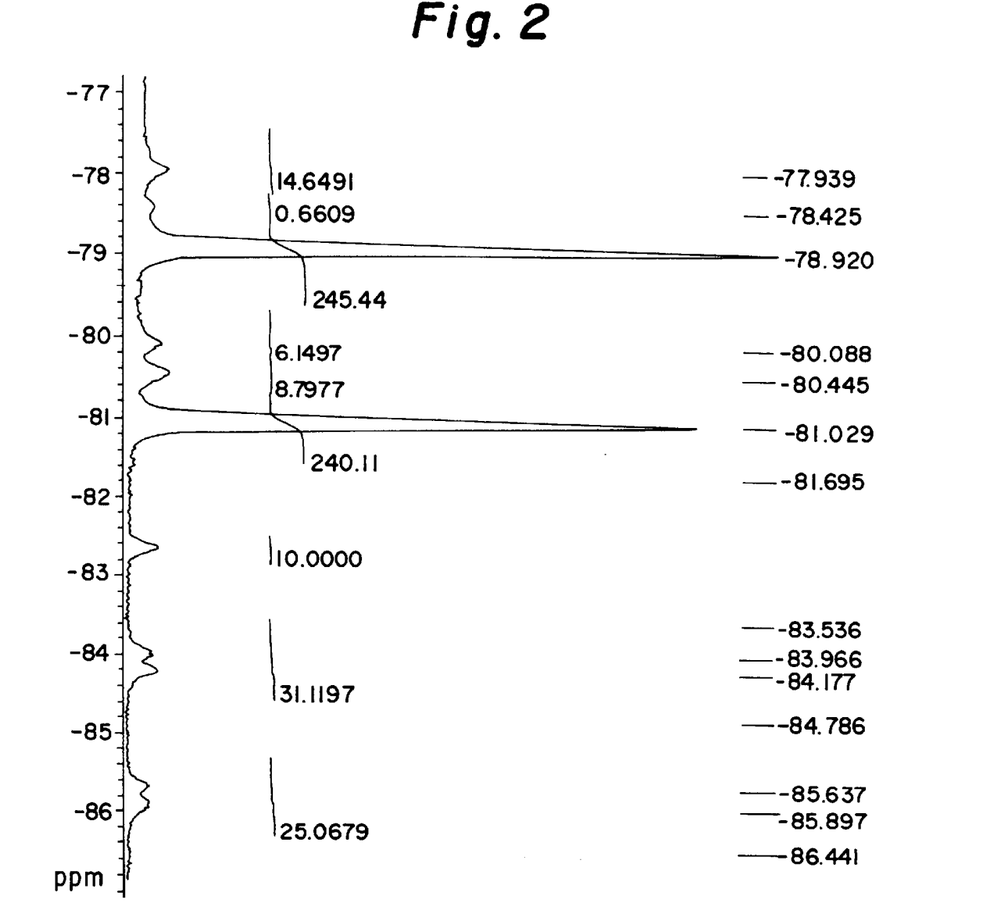
Figure 3:
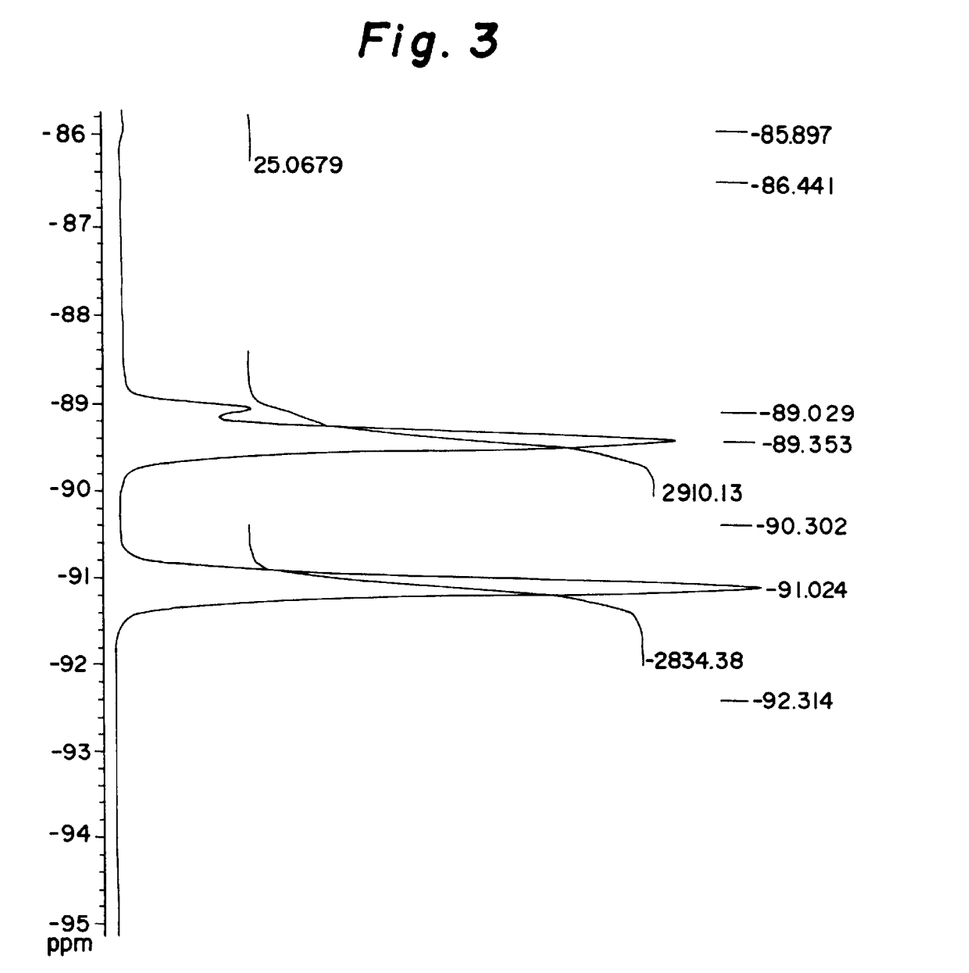
Figure 4:
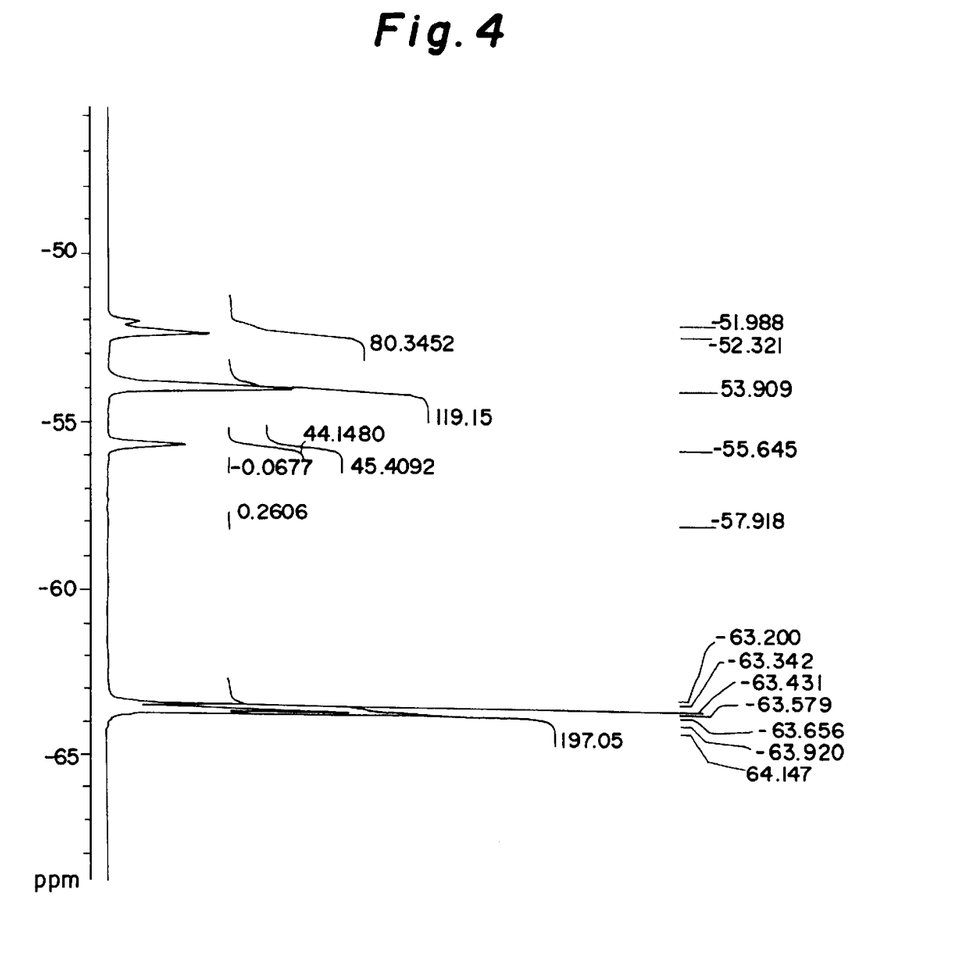
FIGS. 4 to 6 are NMR charts of the compound (5-a).
Figure 5:
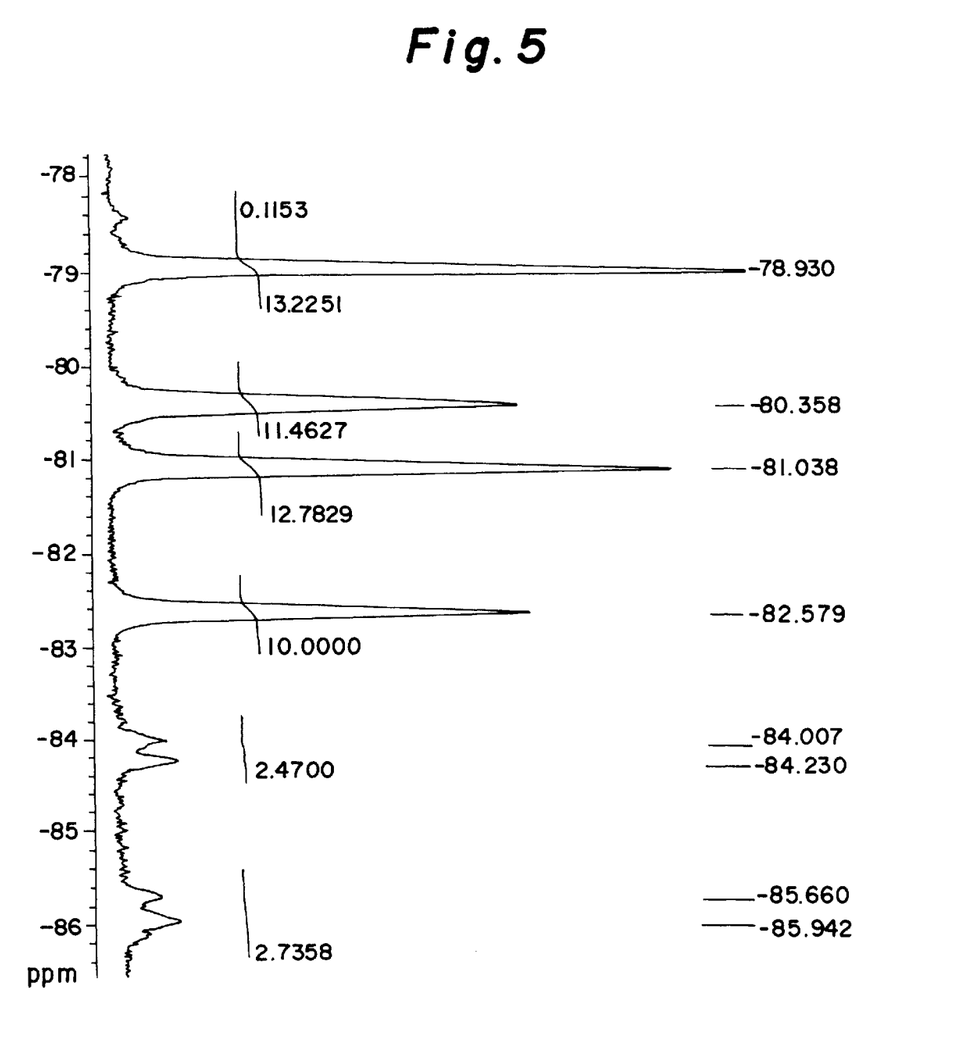
Figure 6:
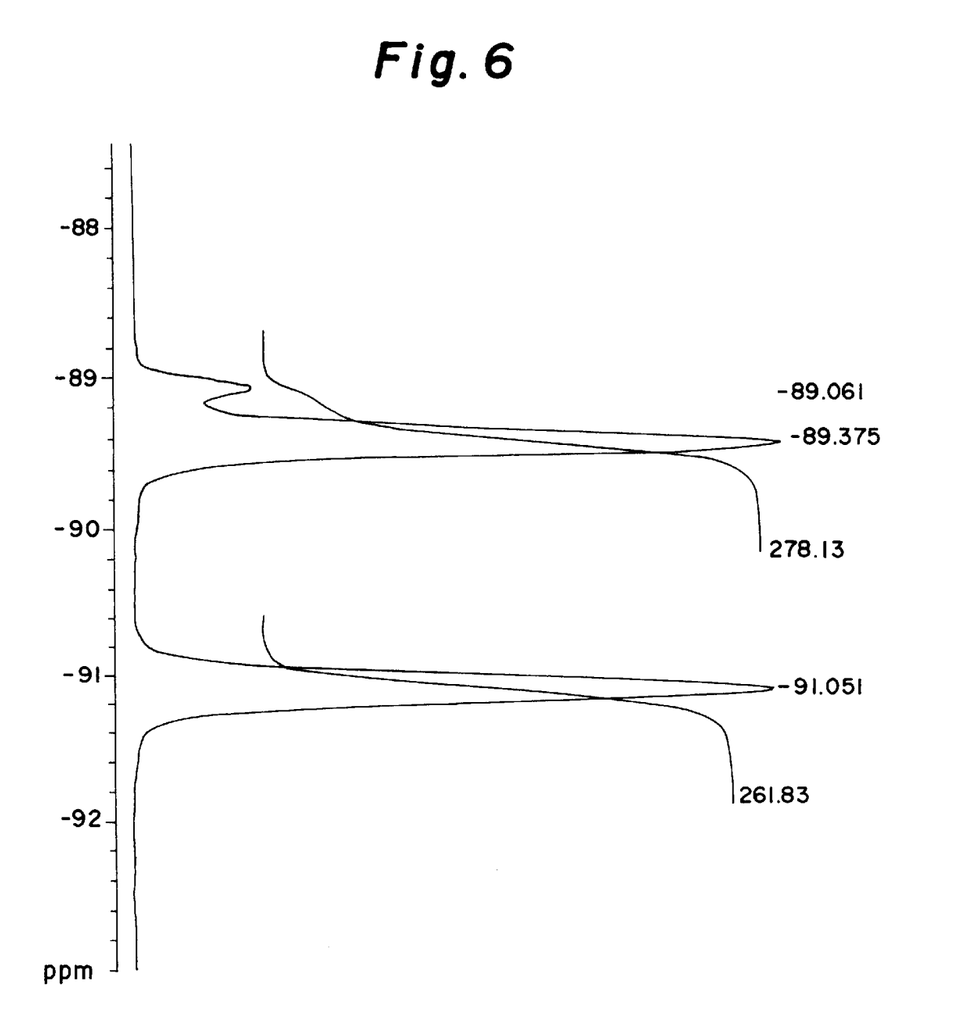

FIGS. 1 to 3 are NMR charts of the compound (1-c).
FIGS. 4 to 6 are NMR charts of the compound (5-a).

EXAMPLE 7

The reaction was conducted in the same manner as in Example 6 except of using meta-phenoxyphenol in place of meta—trifluoromethylphenol to obtain 35 g of compound (1-d) having a cyclotrimer of phosphonitrile wherein 5 meta-phenoxyphenoxy groups substituted on both ends of PFPE-DOH, and 65 g of compound (5-b) having a cyclotrimer of phosphonitrile wherein 5 meta-phenoxyphenoxy groups substituted on one end of PFPE-DOH.

[compound (1-d)], density 1.65 g/cm³(15° C.), boiling point 200° C. or higher/10⁻⁴ torr, viscosity 630 cps (40° C.), surface tension 32 dyne/cm (20° C.).

[compound (5-b)], density 1.71 g/cm³(15° C.), boiling point 200° C. or higher/10⁻⁴ torr, viscosity 375 cps (40° C.), surface tension 24 dyne/cm (20° C.).

EXAMPLE 8

A 0.5-liter 4-necked flask equipped with a reflux condenser, an argon gas inlet tube, a thermometer and a stirrer was charged with 18.3 g (0.11 mole) of meta-trifluoromethylphenol and 0.1 liter of diisopropyl ether which was dried, dehydrated and purified by distillation. Then 2.3 g (0.1 mole) of small pieces of metal sodium was added with stirring. A reaction was conducted at a temperature for refluxing the diisopropyl ether for two days. After confirming that the metal sodium was entirely consumed, 10.8 g (0.03 mole) of cyclotrimer of phosphonitrile chloride was added while stirring the reaction mixture. Thereafter a reaction was made at a refluxing temperature for 3 days to give about 25 g of a reaction mixture. The reaction mixture was washed with about 50 ml of purified water 5 times. Then the diisopropyl ether layer was separated and dehydrated by molecular sieves after which the diisopropyl ether was removed under reduced pressure by distillation with a rotary evaporator, giving a brown transparent liquid, which is hereinafter referred to as "(v)".

A flask of the same type as above was charged with 20 g (0.01 mole) of PFPE-DOH used in Example 6 and 0.23 g (0.01 mole) of small pieces of metal sodium. The mixture was reacted at 50 to 100° C. for 12 days. Then it was confirmed that the metal sodium was entirely consumed in the reaction. Thereafter 45 g of perfluorohexyl methyl ether was added to reduce the viscosity of the reaction mixture. A solution of 2.2 g of the liquid (v) in 14 g of diisopropyl ether was gradually added dropwise to the mixture. After 3-day stirring at a refluxing temperature, the mixture was left to cool to room temperature. The reaction mixture was washed with 1% aqueous solution of nitric acid, purified water and toluene to obtain 18 g of compound.

The obtained compound was identified as the following substance according to proton NMR (400 MHz) and FT-IR:

The compound (5-c) which was a compound having a cyclotrimer of phosphonitrile wherein 3 meta-trifluoromethylphenoxy groups substituted on one end of PFPE-DOH.

Table 1 shows properties of compounds.

TABLE 1

| Compound | viscosity (cps) 40° C. | density (g/cm³) 15° C. | surface tension (dyne/cm) 20° C. |
|---|---|---|---|
| (1-c) | 340 | 1.69 | 31 |
| (5-a) | 110 | 1.75 | 23 |
| (1-d) | 630 | 1.65 | 32 |

TABLE 1-continued

| Compound | viscosity (cps) 40° C. | density (g/cm³) 15° C. | surface tension (dyne/cm) 20° C. |
|---|---|---|---|
| (5-b) | 375 | 1.71 | 24 |
| (5-c) | 850 | 1.75 | 24 |
| (D) | 50 (mm²/sec, 40° C.) | 1.60 | 25.2 (25° C.) |

TEST EXAMPLE 1

The performance test of lubricants was conducted in the same manner as in Example 3 using the compounds of Examples 6 to 8 and Comparative Example 1. The results were given in Tables 2 to 4.

TABLE 2

| | Amount (wt. %) | | | | | | | |
|---|---|---|---|---|---|---|---|---|
| (1-c) | 100 | 95 | 80 | 50 | 20 | 5 | 0 | — |
| (5-a) | 0 | 5 | 20 | 50 | 80 | 95 | 100 | — |
| (D) | — | — | — | — | — | — | — | 100 |
| viscosity (40° C.) (cps) | 340 | 320 | 290 | 190 | 140 | 115 | 110 | 50 (mm²/sec, 40° C.) |
| CSS life (cycles) | 52000 | 87000 | >100000 | >100000 | >100000 | 75000 | 52000 | 28000 |
| occurrence of abrasion | none | none | none | none | none | none | none | trace |

TABLE 3

| | Amount (wt. %) | | | | | | | |
|---|---|---|---|---|---|---|---|---|
| (1-d) | 100 | 95 | 80 | 50 | 20 | 5 | 0 | — |
| (5-b) | 0 | 5 | 20 | 50 | 80 | 95 | 100 | — |
| (D) | — | — | — | — | — | — | — | 100 |
| Viscosity (40° C.) (cps) | 630 | 620 | 590 | 485 | 425 | 380 | 375 | 50 (mm²/sec, 40° C.) |
| CSS life (cycles) | 53000 | 76000 | 80000 | >100000 | >100000 | 70000 | 51000 | 28000 |
| occurrence of abrasion | none | none | none | none | none | none | none | trace |

TABLE 4

| | Amount (wt. %) | | | | | | | |
|---|---|---|---|---|---|---|---|---|
| (1-c) | 100 | 95 | 80 | 50 | 20 | 5 | 0 | — |
| (5-c) | 0 | 5 | 20 | 50 | 80 | 95 | 100 | — |
| (D) | — | — | — | — | — | — | — | 100 |
| Viscosity (40° C.) (cps) | 340 | 360 | 415 | 540 | 710 | 810 | 850 | 50 (mm²/sec, 40° C.) |
| CSS life (cycles) | 52000 | 76000 | 85000 | >100000 | 85000 | 69000 | 55000 | 28000 |
| Occurrence of abrasion | none | none | none | none | none | none | none | trace |

As shown above, CSS durability of magnetic recording media was improved by use of the compounds of the invention as a lubricant.

According to the invention, a compound to be used, for example, as a lubricant for hard disks of excellent CSS durability and a lubricant containing the compound can be prepared.

What is claimed is:

1. A phosphazene compound of the formula (1) which has an arrangement such that perfluoroxyalkylene units selected from —CF$_2$O— and —CF$_2$CF$_2$O— are randomly distributed, the compound having a functional terminal group A $$A—OCH_2CF_2O(CF_2CF_2O)p(CF_2O)qCF_2CH_2O—A \qquad (1)$$

wherein A is a group of the formula (a) shown below, R is a hydrogen atom, $C_{1-4}$ alkyl, $C_{1-4}$ alkoxy, $C_{1-4}$ haloalkyl, aryl, substituted aryl, aryloxy or substituted aryloxy, and p and q are a real number of 1 to 30, and (a) is

(a)

2. A phosphazene compound of the formula (5) which has an arrangement such that perfluoroxyalkylene units selected from —CF$_2$O— and —CF$_2$CF$_2$O— are randomly distributed, the compound having a functional terminal group G $$G\text{—}[OCH_2CF_2O(CF_2CF_2O)p(CF_2O)qCF_2CH_2OH]_{6-z} \quad (5)$$

wherein G is a group of the formula (g) shown below, R is a hydrogen atom, C$_{1-4}$ alkyl, C$_{1-4}$ alkoxy, C$_{1-4}$ haloalkyl, aryl, substituted aryl, aryloxy or substituted aryloxy, and p and q are a real number of 1 to 30, and z is an integer of 1 to 5, and (g) is 3. A phosphazene compound as defined in claim 1 wherein R is aryloxy group.

4. A phosphazene compound as defined in claim 2 wherein R is aryloxy group.

5. A lubricant containing at least one of the phosphazene compounds of the formulas (1) and (5).

6. A lubricant containing at least one of the phosphazene compounds of the formulas (1) and (5), and an oligomer of perfluoroalkyl polyether of the formula (b) having an average molecular weight of 400 to 6000

$$HOCH_2CF_2O(CF_2CF_2O)r(CF_2O)sCF_2CH_2OH \quad (b)$$

wherein r is 1 to 30, and s is 1 to 30.

7. A lubricant containing at least one of the phosphazene compounds of the formulas (1) and (5), and an oligomer of perfluoroalkyl polyether of the formula (c)

$$X\text{—}CF_2O(CF_2CF_2O)m(CF_2O)nCF_2\text{—}Y \quad (c)$$

wherein X and Y are each at least one group selected from HO(CH$_2$CH$_2$O)tCH$_2$—, HOCH$_2$CH(OH)CH$_2$OCH$_2$—, HOOC— and piperonyl, m is 1 to 80, n is 1 to 80, and t is 1 to 30.

8. A lubricant containing at least one of the phosphazene compounds of the formulas (1) and (5), and an oligomer of perfluoroalkyl polyether of the formula (d)

$$F\text{—}[CF(CF_3)CF_2O]uCF(CF_3)COOH \quad (d)$$

wherein u is 1 to 60.

9. A lubricant containing at least one of the phosphazene compounds of the formulas (1) and (5), and a phosphazene compound of the formula (e)

$$[N\text{=}P\{OCH_2CF_2CF_3\}a\{OCH_2(CF_2CF_2)xH\}b]y \quad (e)$$

wherein a and b are each a real number of 0 to 2, a+b=2, x is 1, 2, 3 or 4, and y is 3 or 4.

10. A lubricant as defined in claim 5 wherein the lubricant is a lubricant for a recording medium.

* * * * *